US012805752B2

(12) United States Patent
Motoyoshi et al.

(10) Patent No.: US 12,805,752 B2
(45) Date of Patent: Nov. 24, 2026

(54) DEVICE AND METHOD FOR FOOT SIZE MEASUREMENT

(71) Applicant: ASICS CORPORATION, Kobe (JP)

(72) Inventors: Fumiya Motoyoshi, Kobe (JP); Masayuki Tsutsui, Kobe (JP); Mai Nakaya, Kobe (JP); Justin Paul Garavel, Kobe (JP)

(73) Assignee: ASICS CORPORATION, Kobe (JP)

( * ) Notice: Subject to any disclaimer, the term of this patent is extended or adjusted under 35 U.S.C. 154(b) by 898 days.

(21) Appl. No.: 17/833,620

(22) Filed: Jun. 6, 2022

(65) Prior Publication Data

US 2022/0395194 A1 Dec. 15, 2022

(30) Foreign Application Priority Data

Jun. 11, 2021 (JP) ................................ 2021-097824

(51) Int. Cl.
*A61B 5/107* (2006.01)
*A61B 5/00* (2006.01)

(52) U.S. Cl.
CPC .......... *A61B 5/1074* (2013.01); *A61B 5/1072* (2013.01); *A61B 5/1075* (2013.01); *A61B 5/1079* (2013.01); *A61B 5/7435* (2013.01)

(58) Field of Classification Search
CPC ... A61B 5/1074; A61B 5/1072; A61B 5/1075; A61B 5/1079; A61B 5/7435;
(Continued)

(56) References Cited

U.S. PATENT DOCUMENTS 5,671,055 A 9/1997 Whittlesey et al.
7,668,408 B2 2/2010 Kimura et al.
(Continued)

FOREIGN PATENT DOCUMENTS

JP 2000-509139 A 7/2000
JP 2006-292539 A 10/2006
(Continued)

OTHER PUBLICATIONS

An Office Action mailed by the State Intellectual Property Office of the People's Republic of China on Mar. 20, 2024, which corresponds to Chinese Patent Application No. 202210549198.3 and is related to U.S. Appl. No. 17/833,620.
(Continued)

*Primary Examiner* — Tse Chen
*Assistant Examiner* — Hy Khanh Doan
(74) *Attorney, Agent, or Firm* — Studebaker Brackett PLLC

(57) ABSTRACT

In a foot size measurement system, a measurement unit selectively measures one or more of multiple measurement elements to be measured as feature values defining one foot size, based on a one-foot image of a measured person. An information generator generates foot size information based on one or more measurement elements selectively measured by the measurement unit, among the multiple measurement elements. An output unit outputs the foot size information. The measurement unit selectively measures one or more of multiple measurement elements including a foot width and a foot length of one foot of a measured person.

9 Claims, 13 Drawing Sheets

(58) Field of Classification Search
CPC ..... A61B 5/0077; A61B 5/6898; A61B 5/742; A43D 1/02; A43D 1/025; G06T 7/0002; G06T 7/62; G06T 2207/10004; G06T 2207/30196
See application file for complete search history.

(56) References Cited

U.S. PATENT DOCUMENTS

| | | | | |
|---|---|---|---|---|
| 2014/0237858 | A1* | 8/2014 | Adami | A43B 13/141 36/107 |
| 2018/0160777 | A1* | 6/2018 | Hei | G06T 7/521 |
| 2019/0139252 | A1 | 5/2019 | Zaiss et al. | |
| 2020/0178651 | A1 | 6/2020 | Hei et al. | |

FOREIGN PATENT DOCUMENTS

| | | | |
|---|---|---|---|
| JP | 2007-267996 | A | 10/2007 |
| JP | 2019-045463 | A | 3/2019 |
| JP | 2020-129394 | A | 8/2020 |
| KR | 10-2006-0111088 | A | 10/2006 |
| KR | 10-2020-0031797 | A | 3/2020 |
| WO | 2016/121099 | A1 | 8/2016 |
| WO | 2017/026021 | A1 | 2/2017 |
| WO | 2019/040785 | A1 | 2/2019 |
| WO | 2020/208298 | A1 | 10/2020 |

OTHER PUBLICATIONS

The extended European search report issued by the European Patent Office on Oct. 7, 2022, which corresponds to European Patent Application No. 22176518.3-1015 and is related to U.S. Appl. No. 17/833,620.

"Notice of Reasons for Refusal" Office Action issued in JP 2021-097824; mailed by the Japanese Patent Office on Nov. 26, 2024.

An Office Action mailed by China National Intellectual Property Administration on Mar. 22, 2025, which corresponds to Chinese Patent Application No. 202210549198.3 and is related to U.S. Appl. No. 17/833,620; with English language translation.

* cited by examiner

DEVICE AND METHOD FOR FOOT SIZE MEASUREMENT

BACKGROUND OF THE INVENTION

1. Field of the Invention

The present disclosure relates to a measurement technology using image processing. In particular, the present disclosure relates to a method for measuring foot size of a measured person.

2. Description of the Related Art

Wearing shoes of inappropriate size for one's feet not only makes walking difficult, but may also affect one's health. In recent years, purchase of shoes through online shopping has become common but, unlike in-store purchases, many people purchase shoes without trying them on. If more people purchase shoes of inappropriate sizes as a result of purchasing without trying them on, it will lead to an increase in returns. Therefore, allowing purchasers to make purchases based on proper foot size measurement is desirable.

Meanwhile, a system is known to calculate foot size and shoe size based on an image of the foot taken by a customer using a mobile terminal (see Patent Literature 1, for example).

Patent Literature 1: Japanese Unexamined Patent Application Publication No. 2019-45463

In the technology of Patent Literature 1, however, the foot size is measured and displayed after all the image shooting is completed, so that the measured person cannot know the foot size until all the image shooting is completed. Therefore, even if an image shooting error or a measurement error has occurred in some parts, the error could not be recognized until the end. Accordingly, all the image shooting would need to be performed again from the beginning to measure the foot size, for example, which has been inconvenient.

SUMMARY OF THE INVENTION

The present disclosure has been made in view of such a situation, and a purpose thereof is to provide a technology for improving foot size measurement efficiency.

In response to the above issue, a foot size measurement device according to one aspect of the present invention includes: a measurement unit that selectively measures one or more of multiple measurement elements to be measured as feature values defining one foot size, based on a one-foot image of a measured person; an information generator that generates foot size information based on one or more measurement elements selectively measured by the measurement unit, among the multiple measurement elements; and an output unit that outputs the foot size information.

The "multiple measurement elements" may be, for example, measurable elements, such as the foot width, foot length, ball girth, heel width, foot height, heel inclination angle, hallux abduction angle, and arch height of one foot. Also, the "measurement based on the one-foot image" may be processing for obtaining the length or size of each measurement element by comparison with a predetermined reference object through image processing. For the comparison, the "one-foot image" may be shot by a measured person such that the predetermined reference object to be compared appears in the "one-foot image". According to this aspect, one or more of the multiple measurement elements can be selected and measured, and, based on the one or more measurement elements, the foot size information can be generated, so that the foot size measurement efficiency can be improved.

When the number of measurement elements that have been selectively measured by the measurement unit among the multiple measurement elements is more than one, the information generator may generate, as the foot size information, content that depends on a combination of the measured measurement elements. The measurement unit may selectively measure one or more of multiple measurement elements including a foot width and a foot length of one foot of a measured person. The information generator may include, in the foot size information, information regarding the measured element when only one of the foot width and the foot length has been measured and may include, in the foot size information, evaluation information regarding the wideness of the foot width with respect to the foot length, in addition to information regarding the measured elements, when both the foot width and the foot length have been measured. The "evaluation information" may be information related to wideness or narrowness of a foot width with respect to a foot length, for example. According to this aspect, at the time when one or more measurement elements are shot, the measurement elements are measured and displayed, and, in addition, when other measurement elements are shot, information that can only be obtained by combining the measurement elements can be immediately displayed, thereby enhancing the convenience.

The measurement unit may be capable of selectively re-measuring a measured element among the multiple measurement elements. Also, when one or more measurement elements are re-measured by the measurement unit, the information generator may re-generate the foot size information based on one or more measurement elements including the one or more re-measured measurement elements. In this case, when the number of measured measurement elements after the re-measurement is one, the foot size information may be re-generated based on the one measurement element; when the number of measured measurement elements after the re-measurement is more than one, the foot size information may be re-generated based on a combination of the multiple measurement elements. According to this aspect, the measured person can select one or more measurement elements for re-shooting and re-measurement and need not waste past measurements by measuring all the measurement elements again from the beginning, enabling efficient measurement.

Another aspect of the present invention relates to a foot size measurement method. The method includes: measuring selectively one or more of multiple measurement elements to be measured as feature values defining one foot size, by image processing based on a one-foot image of a measured person; generating, by predetermined arithmetic processing, foot size information based on one or more measurement elements selectively measured in the measuring, among the multiple measurement elements; and outputting the foot size information by a predetermined output means. According to this aspect, one or more of the multiple measurement elements can be selected and measured, and, based on the one or more measurement elements, the foot size information can be generated, so that the foot size measurement efficiency can be improved.

Optional combinations of the aforementioned constituting elements, and implementation of the present disclosure, including the constituting elements and expressions, in the form of methods, apparatuses, programs, transitory or non-transitory storage medium storing programs, or systems may also be practiced as additional modes of the present disclosure.

BRIEF DESCRIPTION OF THE DRAWINGS

Embodiments will now be described, by way of example only, with reference to the accompanying drawings which are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

In the following, a foot size measurement system and a foot size measurement program will be illustratively described. The foot size measurement system and the foot size measurement program in the present embodiment allow measurement while multiple measurement elements to be measured as feature values defining foot size can be freely selected, thereby improving the flexibility and efficiency of the size measurement.

Figure 1:
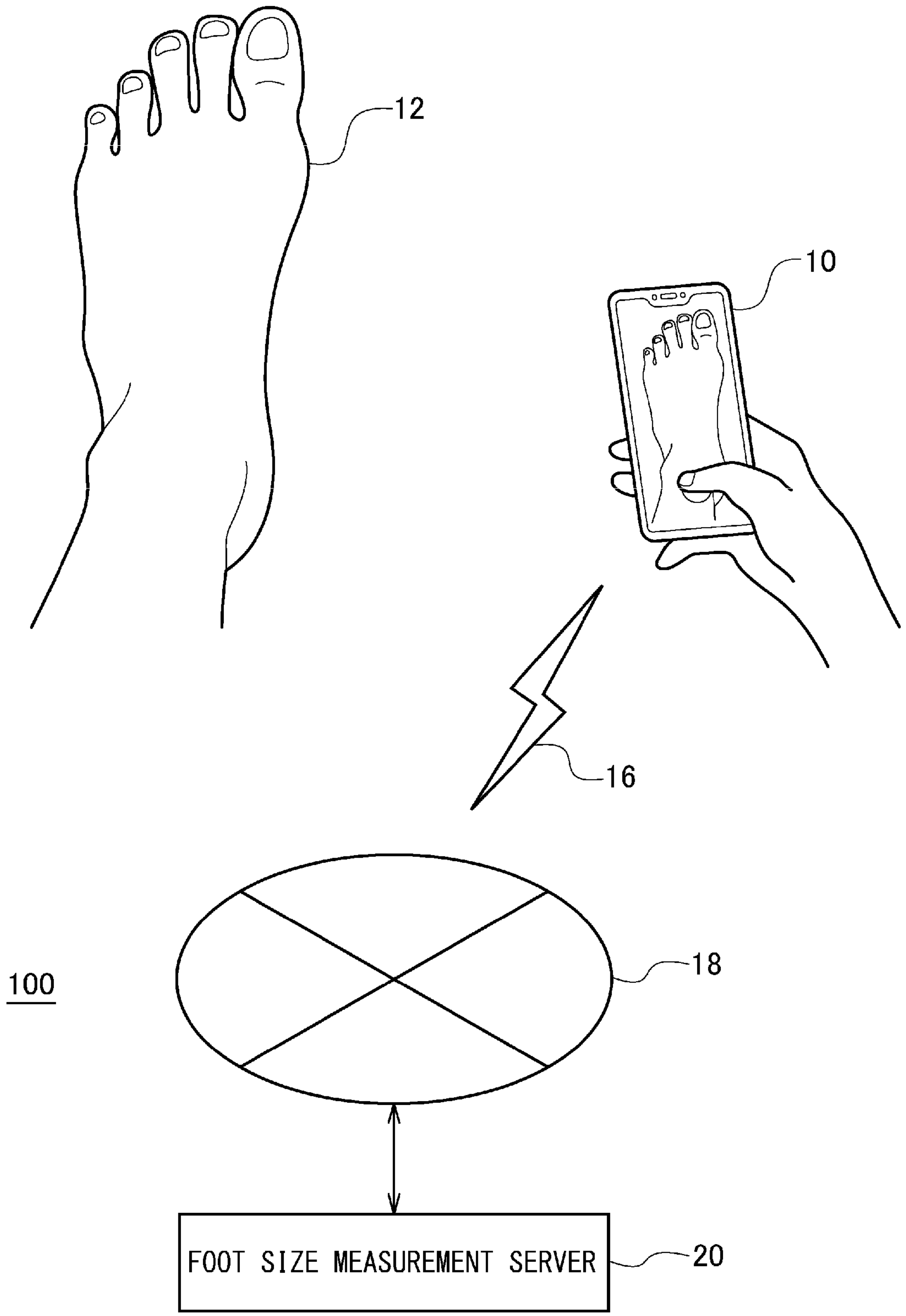
FIG. 1 is a basic configuration diagram of a foot size measurement system.

FIG. 1 is a basic configuration diagram of a foot size measurement system. A foot size measurement system 100 includes a user terminal 10 and a foot size measurement server 20 connected to each other via wireless communication 16 and a network 18. A measured person shoots one of his or her own feet (foot 12) using a camera function of the user terminal 10 and sends the shot image to the foot size measurement server 20 via the wireless communication 16 and the network 18. Based on the received one-foot image, the foot size measurement server 20 measures the foot size and transmits foot size information including the measurement result and evaluation information to the user terminal 10 to display the foot size information on the screen of the user terminal 10.

Each of the user terminal 10 and the foot size measurement server 20 may be constituted by a mobile terminal or a computer including a central processing unit (CPU), a graphics processing unit (GPU), a random access memory (RAM), a read only memory (ROM), an auxiliary storage device, a display device, a communication device, and the like, and by a program stored in the mobile terminal or computer. For example, a program executed on the foot size measurement server 20 side may be used from the user terminal 10 side via the network 18. Also, the foot size measurement system may be implemented by a stand-alone device equipped with all the functions of the user terminal 10 and the foot size measurement server 20, and a measured person may be able to directly operate the stand-alone device to execute the foot size measurement program. The stand-alone device may be provided in the form of, besides a personal computer, a mobile terminal, such as a smartphone, or a tablet terminal, along with a program stored in the computer or terminal. Alternatively, the device may be implemented in the form of a terminal installed in a shoe store and operated by an assistant such as a salesperson, along with a program stored in the terminal.

In the present embodiment, the multiple measurement elements to be measured as feature values defining one foot size may be the foot width and foot length of a foot, for example. Since the foot width and foot length are measured for each of the left and right feet, up to a maximum of four measurement elements are to be measured. However, the measured person may select and measure only some of the multiple measurement elements and check the foot size. In a modification, the multiple measurement elements may further include the ball girth instead of or in addition to the foot width. The measured person selects one of the left and right foot widths and foot lengths to shoot an image therefor using the user terminal 10 and obtains the measurement result. If the measured person desires to know only some of the measurement elements, the measured person may terminate the process after the image shooting and measurement of the some measurement elements is completed. Alternatively, the measured person may terminate the process after the image shooting and measurement of all the four measurement elements is completed. Also, an arbitrary measurement element that has been measured once may be re-shot and re-measured. Therefore, even if an image shooting error or a measurement error is found in some measurement elements, only such measurement elements may be re-shot and re-measured, and re-shooting of all the measurement elements is unnecessary.

Figure 2:
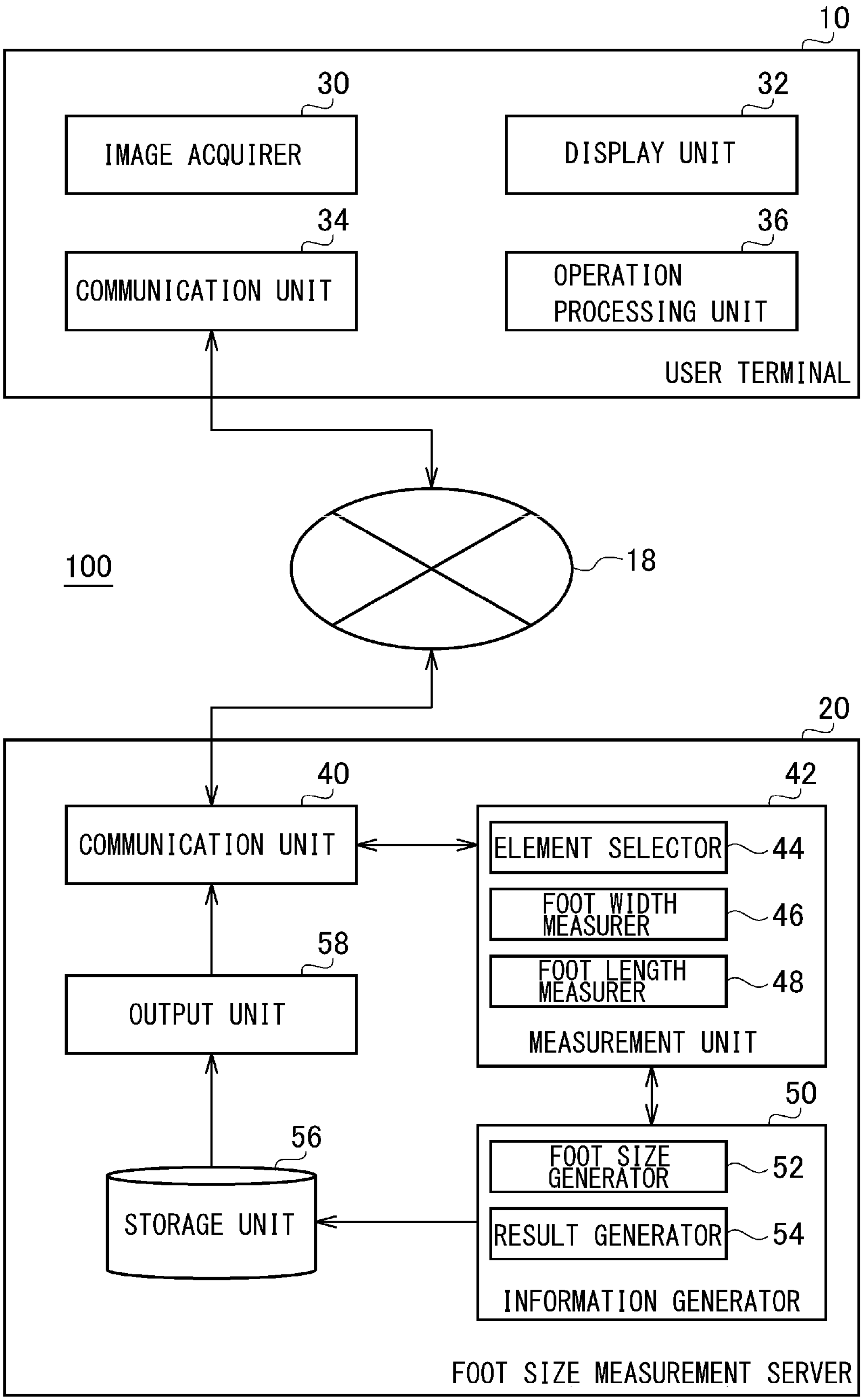
FIG. 2 is a functional block diagram that shows basic configurations of a user terminal and a foot size measurement server.

FIG. 2 is a functional block diagram that shows basic configurations of the user terminal 10 and the foot size measurement server 20. FIG. 2 is a block diagram featuring the functions, and these functional blocks may be implemented in a variety of forms by hardware, software, or a combination thereof.

The user terminal 10 includes an image acquirer 30, a display unit 32, a communication unit 34, and an operation processing unit 36. The operation processing unit 36 accepts operation input from a measured person. The operation processing unit 36 accepts an instruction from the measured person for the start of a series of processes in the foot size measurement program. Based on the instruction, the display unit 32 starts screen display of contents of the foot size measurement program and displays contents related to the measurement procedure. The operation processing unit 36 and the display unit 32 may be constituted by a touch panel, for example, in terms of hardware.

The display unit 32 displays, as options for the multiple measurement elements to be measured, the left foot width, left foot length, right foot width, and right foot length, with images and character strings. The operation processing unit 36 accepts from the measured person an instruction regarding which of the multiple measurement elements to perform image shooting and measurement for. Based on the selection instruction from the operation processing unit 36, the display unit 32 displays shooting procedure for the selected measurement element.

The image acquirer 30 captures an image of one foot of the measured person to acquire a one-foot image. The image acquirer 30 may be constituted by a camera module, for example, in terms of hardware. The communication unit 34 transmits the one-foot image to the foot size measurement server 20 via the network 18 and receives the measurement results and evaluation information from the foot size measurement server 20 to transmit the results and information to the display unit 32. The communication unit 34 may be constituted by a wireless communication module for wireless LAN communication or cellular phone communication, for example, in terms of hardware. The display unit 32 displays, on the screen, the one-foot image of the measured person, the size of the one foot as the measurement results, and the evaluation information.

The foot size measurement server 20 includes a communication unit 40, a measurement unit 42, an information generator 50, a storage unit 56, and an output unit 58. The communication unit 40 receives a one-foot image from the user terminal 10 and transmits the measurement results and evaluation information, which will be described later, to the user terminal 10. The communication unit 40 may be constituted by a communication module for a wired LAN, for example, in terms of hardware.

The measurement unit 42 selectively measures one or more of the multiple measurement elements to be measured as feature values defining one foot size, based on the one-foot image of the measured person. The measurement unit 42 includes an element selector 44, a foot width measurer 46, and a foot length measurer 48.

The element selector 44 transmits, to the user terminal 10 via the communication unit 40, a selection screen on which one of the multiple measurement elements is selected and receives an instruction from the user terminal 10 to select one of the multiple measurement elements as a measurement target. When the element selector 44 receives a measurement instruction for a measurement element that has already been measured among the multiple measurement elements, the element selector 44 selects the indicated measurement element as a re-measurement target.

When the measurement target is the left foot width or the right foot width, the foot width measurer 46 transmits, to the user terminal 10 via the communication unit 40, a screen for describing a procedure regarding image shooting for the left foot width or the right foot width and acquires a one-foot image of the left foot or the right foot captured by the user terminal 10. The one-foot image shows one foot along with a predetermined reference object as described below. The "reference object" is an object to be captured together with one foot in the image, as a comparison object used to measure the foot width or foot length of the one foot based on the image, and is a planar or three-dimensional object of which the size and shape are defined in advance. The "reference object" may be a general-purpose product as long as the size and shape thereof are defined or may be an exclusive product of which the size and shape are defined exclusively for the measurement in the present embodiment. As a reference object in the present embodiment, a planar object of predefined size and shape, such as A4 size (210 mm×297 mm) paper, may be used. The color of the paper may preferably be white but may be another color. It is premised that a one-foot image in the present embodiment is obtained by shooting one foot along with the entire A4 white paper as the reference object on which the one foot is placed. It is also premised that the A4 white paper is placed on a non-white floor during a shoot, so that the A4 white paper can be accurately extracted from the one-foot image by image recognition. The foot width measurer 46 extracts the reference object from the one-foot image and measures the size of the foot width based on comparison with the reference object. As a modification, the foot width measurer 46 may determine, by image recognition, whether or not the one foot in the one-foot image is wearing a sock. Upon judging that the foot is wearing a sock, the foot width measurer 46 may estimate the foot width with the thickness of the sock taken into consideration.

When the measurement target is the left foot length or the right foot length, the foot length measurer 48 transmits, to the user terminal 10 via the communication unit 40, a screen for describing a procedure regarding image shooting for the left foot length or the right foot length and acquires a one-foot image of the left foot or the right foot captured by the user terminal 10. The foot length measurer 48 extracts the reference object (such as A4 white paper) from the one-foot image and measures the size of the foot length based on comparison with the reference object. As a modification, the foot length measurer 48 may determine, by image recognition, whether or not the one foot in the one-foot image is wearing a sock. Upon judging that the foot is wearing a sock, the foot length measurer 48 may estimate the foot length with the thickness of the sock taken into consideration.

The information generator 50 generates foot size information based on the measurement result of one or more measurement elements selectively measured by the measurement unit 42, among the multiple measurement elements, and stores the foot size information in the storage unit 56. The stored foot size information is transmitted to the user terminal 10 via the output unit 58. The information generator 50 includes a foot size generator 52 and a result generator 54.

The foot size generator 52 generates foot size information including the measurement results of some or all of the measurement elements selectively measured by the measurement unit 42. For example, when only some measurement elements have been measured, foot size information that only includes the size of the some measurement elements is generated. When the number of elements that have been selectively measured among the multiple measurement elements is more than one, the result generator 54 generates foot size information that includes evaluation information of which content depends on the combination of the measured measurement elements. When both the foot width and the foot length of either the left or right foot are measured, for example, the evaluation information may relate to wideness or narrowness of the foot width with respect to the foot length; for example, when the foot width is wider or narrower by a predetermined percentage or more than an average of the foot width for the same foot length, the evaluation information may include the evaluation of "wider than average" or "narrower than average".

When a measured measurement element is re-shot and re-measured by the measurement unit 42, the foot size generator 52 re-generates the foot size information based on one or more measurement elements including the re-measured measurement element and updates or overwrites and saves the foot size information before the re-measurement.

Figure 3:
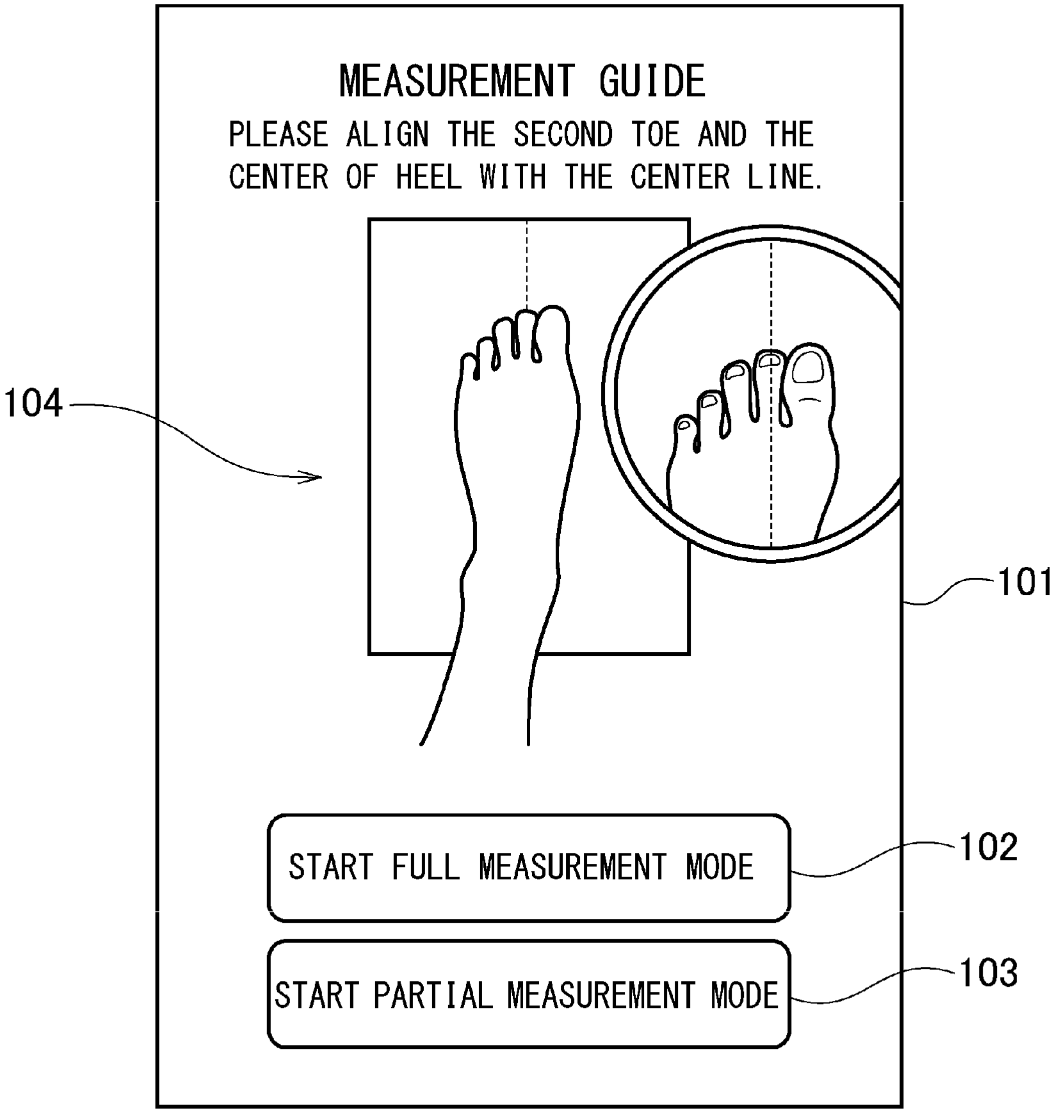
FIG. 3 illustrates an example of a screen shown before the start of image shooting and measurement.

FIG. 3 illustrates an example of a screen shown before the start of image shooting and measurement. First, when a measured person starts operation of the foot size measurement system, a start screen 101 including an explanation column 104, a first start button 102, and a second start button 103 is displayed as a measurement guide as shown in FIG. 3. The explanation column 104 shows, with the display of an image such as animation and a character string, content that prompts the measured person to prepare A4-size white paper as the reference object and also to fold the white paper in half vertically and establish a center line at the folded line. Subsequently, the explanation column 104 shows instructions to place the white paper on a flat floor and to avoid a white floor or a dark area so as not to make the recognition of the boundary between the white paper and the floor difficult. Also, the explanation column 104 further shows an instruction indicating that, when the foot is illuminated, the medial side rather than the lateral side of the foot should be illuminated so as to avoid shadows on the medial side. Thereafter, the explanation column 104 indicates that the measured person should place a foot, with the sock taken off and the hem of the cloth lifted up to around the knee, on the white paper and align the second toe and the center of the heel with the center line of the white paper. As a procedure for image shooting for the foot width, the explanation column 104 indicates that the measured person should stand and hold a camera of the user terminal 10 directly above the foot to shoot the foot. Also, as a procedure for image shooting for the foot length, the explanation column 104 indicates that the measured person should stand on one knee and hold a camera of the user terminal 10 over the medial side of the foot to shoot the foot.

To select and execute a "full measurement mode" in which all of the multiple measurement elements are shot in a predetermined order to be measured, the measured person presses the first start button 102. Meanwhile, to select and execute a "partial measurement mode" in which one or more of the multiple measurement elements are selected and shot in an arbitrary order to be measured, the measured person presses the second start button 103. In the following, the partial measurement mode executed when the second start button 103 is pressed will be described, and the explanation of the full measurement mode executed when the first start button 102 is pressed will be omitted. The present embodiment describes, as an example, a method in which the foot size measurement procedures in the full measurement mode and the partial measurement mode are provided and the measured person selects one of the modes. However, a modification may employ a method in which the full measurement mode is omitted, i.e., a method in which the measured person selects a measurement target each time, as in the partial measurement mode. Alternatively, a method may be employed in which, after all the measurement elements are measured once in the full measurement mode, the partial measurement mode is executed only when some of the measurement elements are to be re-measured. Alternatively, a method may be employed in which the full measurement mode is automatically started without requesting the mode selection from the measured person, and the partial measurement mode is executed only when the measured person performs a predetermined operation to order the partial measurement mode during the full measurement mode.

Figure 4:
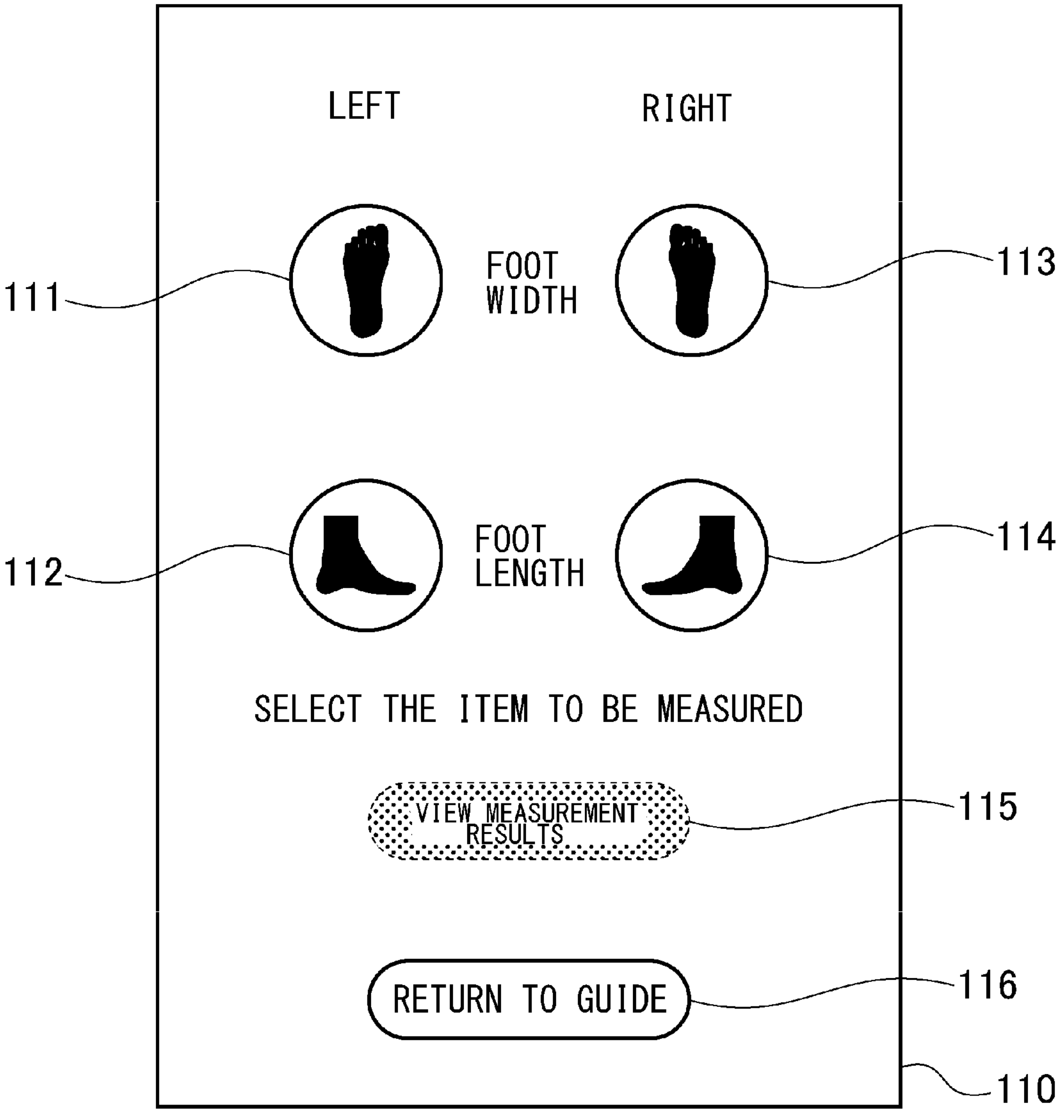
FIG. 4 illustrates an example of a screen on which the target of image shooting and measurement is selected.

FIG. 4 illustrates an example of a screen on which the target of image shooting and measurement is selected. A selection screen 110 shows a first element selection button 111 corresponding to the left foot width, a second element selection button 112 corresponding to the left foot length, a third element selection button 113 corresponding to the right foot width, and a fourth element selection button 114 corresponding to the right foot length. As the first element selection button 111, a pictogram icon depicting a left foot viewed from directly above is displayed. As the second element selection button 112, a pictogram icon depicting a left foot viewed from a side is displayed. As the third element selection button 113, a pictogram icon depicting a right foot viewed from directly above is displayed. As the fourth element selection button 114, a pictogram icon depicting a right foot viewed from a side is displayed. The measured person can select an element to measure by selectively pressing one of the first element selection button 111, the second element selection button 112, the third element selection button 113, and the fourth element selection button 114.

A result display button 115 is a button used for shifting to a screen displaying a measurement result; however, before the measurement, the button is grayed out and the pressing thereof is disabled. A guide display button 116 is a button used to order the returning to the start screen 101 shown in FIG. 3.

Figure 5:
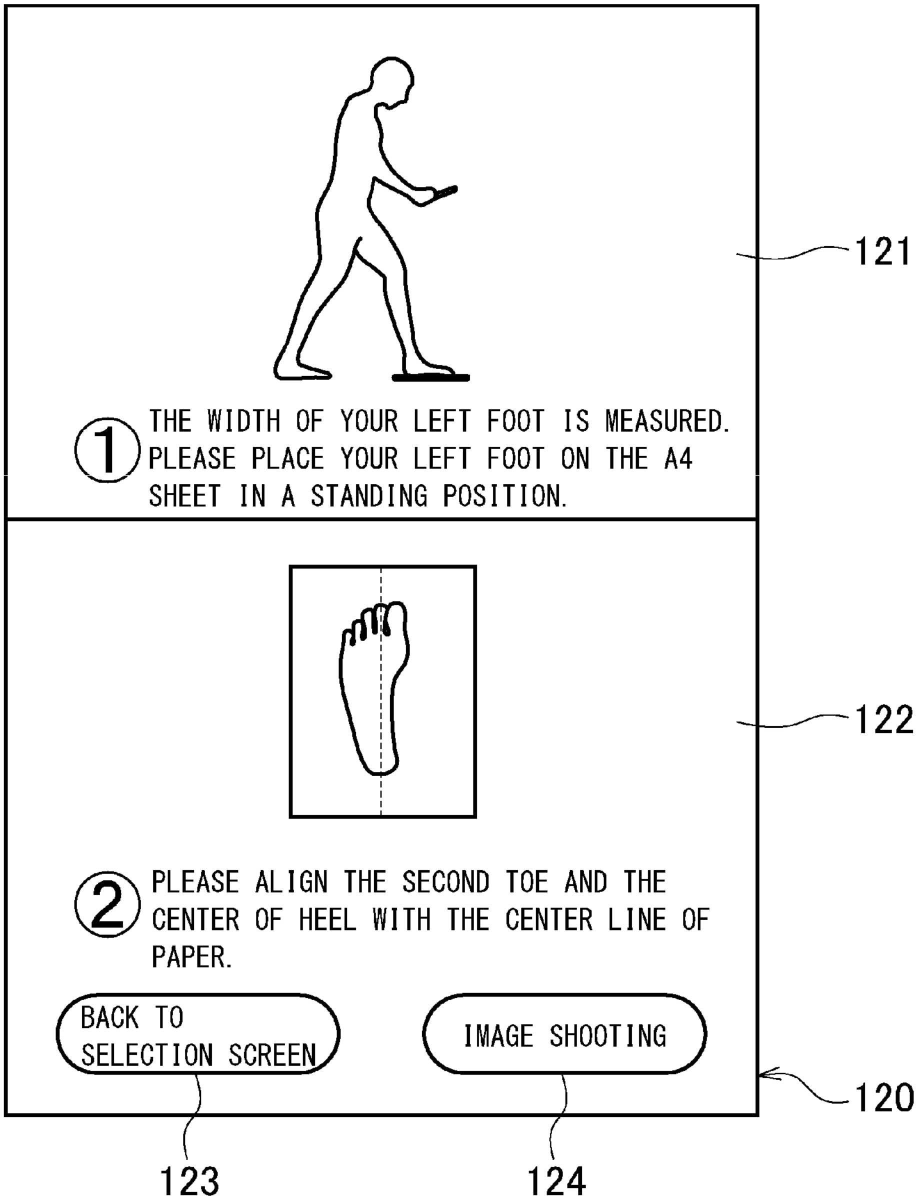
FIG. 5 illustrates an example of a screen for describing a procedure for measuring a left foot width.

FIG. 5 illustrates an example of a screen for describing a procedure for measuring the left foot width. An explanation screen 120 includes a first explanation column 121, a second explanation column 122, a back button 123, and an image shooting shift button 124. The first explanation column 121 shows a character string such as "The width of your left foot is measured. Please place your left foot on the A4 sheet in a standing position." and also shows an image illustrating a posture of a measured person for image shooting. The second explanation column 122 shows a character string such as "Please align the second toe and the center of the heel with the center line of the paper." and also shows an image illustrating the positional relationship between the A4 sheet and the foot. When the measured person presses the back button 123, the image shooting is stopped, and the screen returns to the selection screen 110 shown in FIG. 4. When the measured person presses the image shooting shift button 124, the screen shifts to an image shooting screen shown in FIG. 6. Also when the right foot width is measured, similar explanation is displayed.

Figure 6:
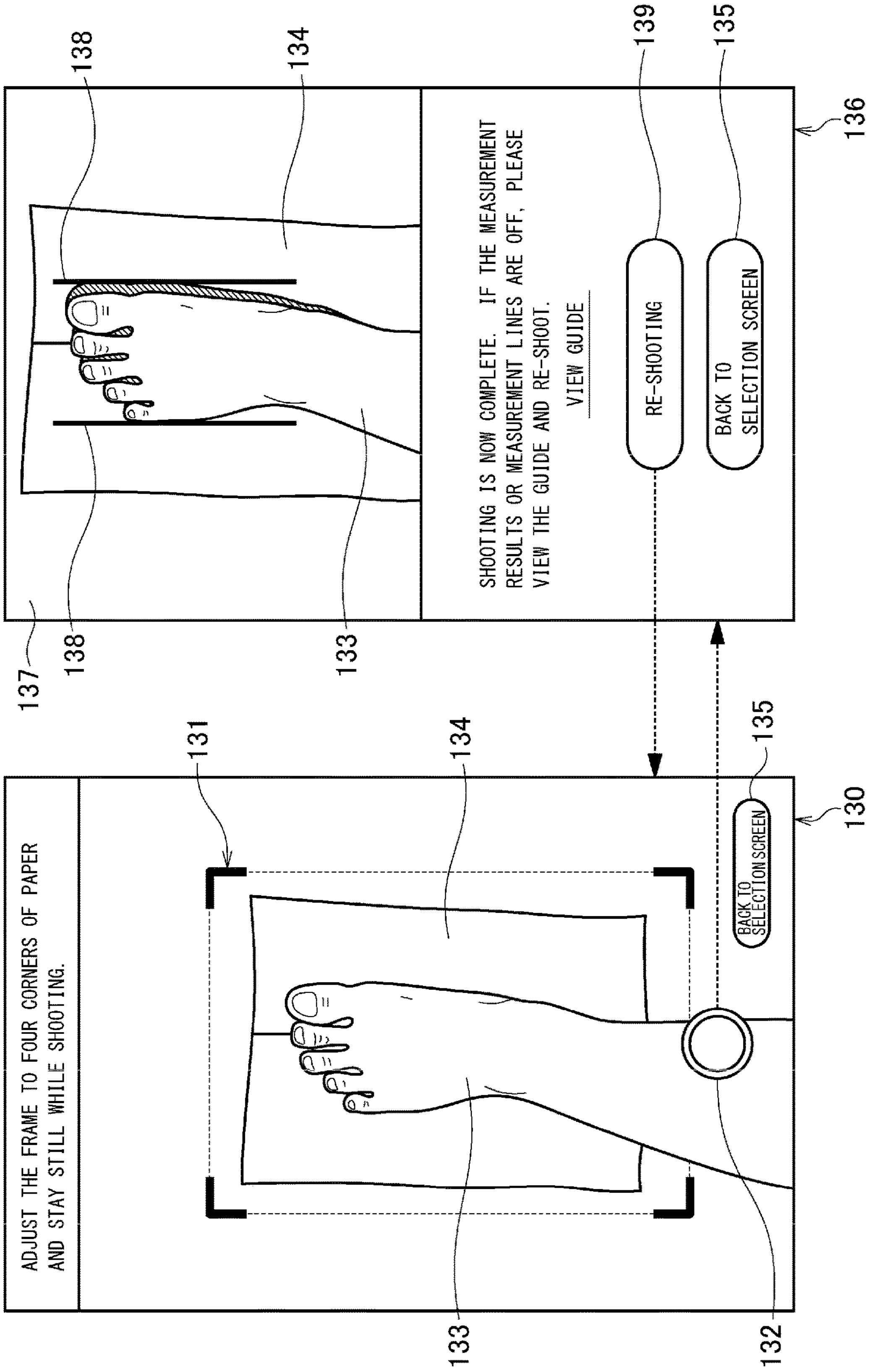
FIG. 6 illustrates an image shooting screen for the left foot width.

FIG. 6 illustrates an image shooting screen for the left foot width. On the entirety of an image shooting screen 130, a live view image captured by the camera of the user terminal 10 is displayed, and, on the live view image, a frame image 131 and a shutter button 132 are superimposed. The frame image 131 corresponds to auxiliary frame lines that indicate an appropriate shape and size of white paper 134 as the reference object so that the white paper 134 can be set to appear in the image in the appropriate shape and size. As the live view image, an image of a foot 133 of the measured person placed on the white paper 134 is displayed on the image shooting screen 130, and the measured person adjusts the distance between the camera and the foot or the angle of view so that the white paper 134 is positioned to almost match the frame image 131. When the measured person presses the shutter button 132, the image acquirer 30 performs shutter operation to acquire a one-foot image, and the screen shifts to a shooting result screen 136 shown on the right in FIG. 6. When the measured person presses a back button 135, the screen returns to the selection screen 110 shown in FIG. 4.

The image acquirer 30 may recognize the shape and the ratio of two sides of the white paper 134 as the reference object on the image and may perform shutter operation to acquire a one-foot image upon recognition of satisfying a predetermined condition indicating that the image contains the reference object of appropriate shape and size. The predetermined condition indicating that the image contains the reference object of appropriate shape and size may be, for example, a condition that defines a rectangular shape and a ratio of two sides thereof assumed to be obtained when the white paper 134 as the reference object is shot from directly above. Also when the image shooting for the right foot width is performed, similar screens are displayed and image shooting is performed following a similar procedure.

The shooting result screen 136 shows a one-foot image 137 in an upper center part thereof and also shows measurement support lines 138, which are two vertical lines positioned respectively at the left and right ends of the instep of the foot 133 recognized by the foot width measurer 46 based on the one-foot image 137. The one-foot image 137 illustrated in FIG. 6 shows a case where a dark shadow appears to the right of the foot 133 and the foot width measurer 46 misidentifies the right end of the shadow as the right end of the foot 133. When such misidentification has occurred or when the measured person desires re-shooting for a clearer image, by pressing a re-shooting button 139, the measured person can return to the image shooting screen 130 again to perform re-shooting. When there is no problem with the one-foot image 137, the measured person presses the back button 135 to shift to the selection screen 110 shown in FIG. 4.

Figure 7:
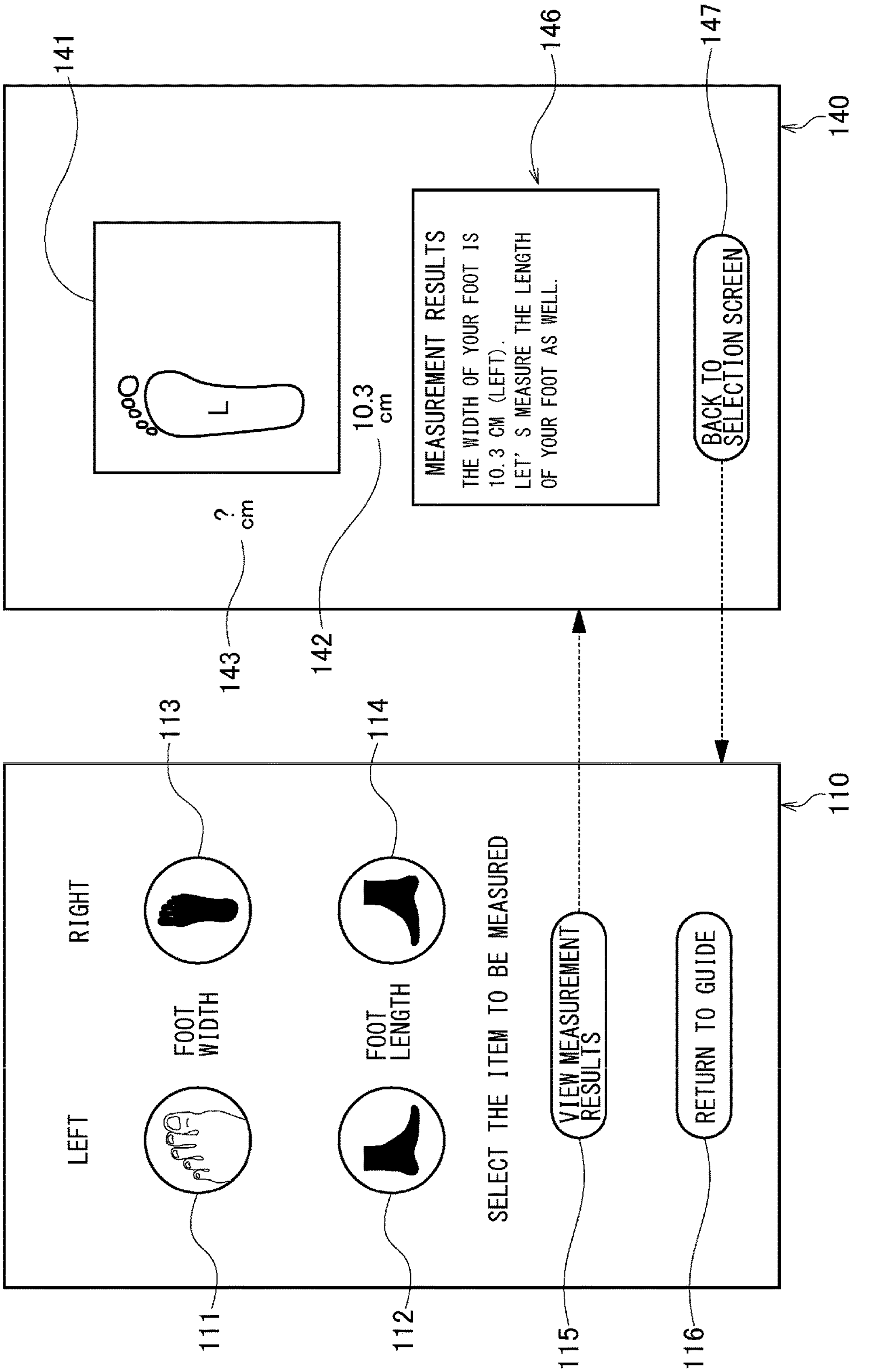
FIG. 7 illustrates a selection screen and a measurement result screen shown after the image shooting for the left foot width is performed.

FIG. 7 illustrates the selection screen and a measurement result screen shown after the image shooting for the left foot width is performed. On the selection screen 110 in FIG. 7, among the four selection buttons, only the first element selection button 111, for which image shooting has been performed, is displayed in the form of a thumbnail of the captured image, instead of the pictogram. This allows the measured person to visually recognize that the image shooting for the left foot width has been performed. Also, unlike the selection screen 110 of FIG. 4 before the image shooting, the result display button 115 is displayed without the grayout and the pressing thereof is made valid. When the measured person presses the result display button 115, the screen shifts to a measurement result screen 140 shown on the right in FIG. 7.

The measurement result screen 140 is a screen that shows the measurement results and evaluation information as foot size information. On the measurement result screen 140, a foot figure column 141 is displayed in an upper center part, a comment column 146 is displayed in a lower center part, and a back button 147 is displayed further therebelow. The foot figure column 141 at the time as shown in FIG. 7 only shows a picture of the left foot, indicating that measurement thereof has been performed. As areas where the measurement results of the measurement elements are respectively displayed, a left foot width column 142 is displayed on the lower left side of the foot figure column 141, and a left foot length column 143 is displayed on the left side of the foot figure column 141. Initially, each of the left foot width column 142 and the left foot length column 143 is filled with a unit with no numerical value, such as "? cm", for the foot width or the foot length. After the measurement of each measurement element, for the measured foot width or foot length, the numerical value of the measurement result is displayed in the left foot width column 142 or the left foot length column 143. Since the left foot width has already been measured in the example of FIG. 7, a numerical value such as "10.3 cm" is displayed in the left foot width column 142.

In the comment column 146, the evaluation information is displayed. For example, the comment column 146 shows a character string, such as "The width of your foot is 10.3 cm (left). Let's measure the length of your foot as well." Since whether the foot width is wider or narrower than average is determined by the contrast between the foot length and the foot width, the wideness of the foot width cannot be technically evaluated at the time when only the foot width has been measured and the foot length has not been measured yet. Therefore, when either the foot width or the foot length has not been measured, initial content as shown in FIG. 7 is displayed. Thereafter, at the time when the foot length of the same foot is measured, the display of the comment column 146 can be changed.

When the measured person presses the back button 147, the screen returns to the selection screen 110 shown on the left in FIG. 7.

On the selection screen 110, when the measured person presses the first element selection button 111, which indicates that measurement therefor has been performed, the screen shifts to a re-shooting screen for the left foot width, and the measured person can perform re-shooting and re-measurement. Meanwhile, if the measured person only desires the measurement of the left foot width, the measured person may finish the measurement at this point. In the following, an example of a case will be described in which, subsequent to the measurement of the left foot width, image shooting and measurement for the right foot width is also performed. Since the shooting method for the right foot width is the same as illustrated in FIGS. 5 and 6, the description thereof will be omitted.

Figure 8:
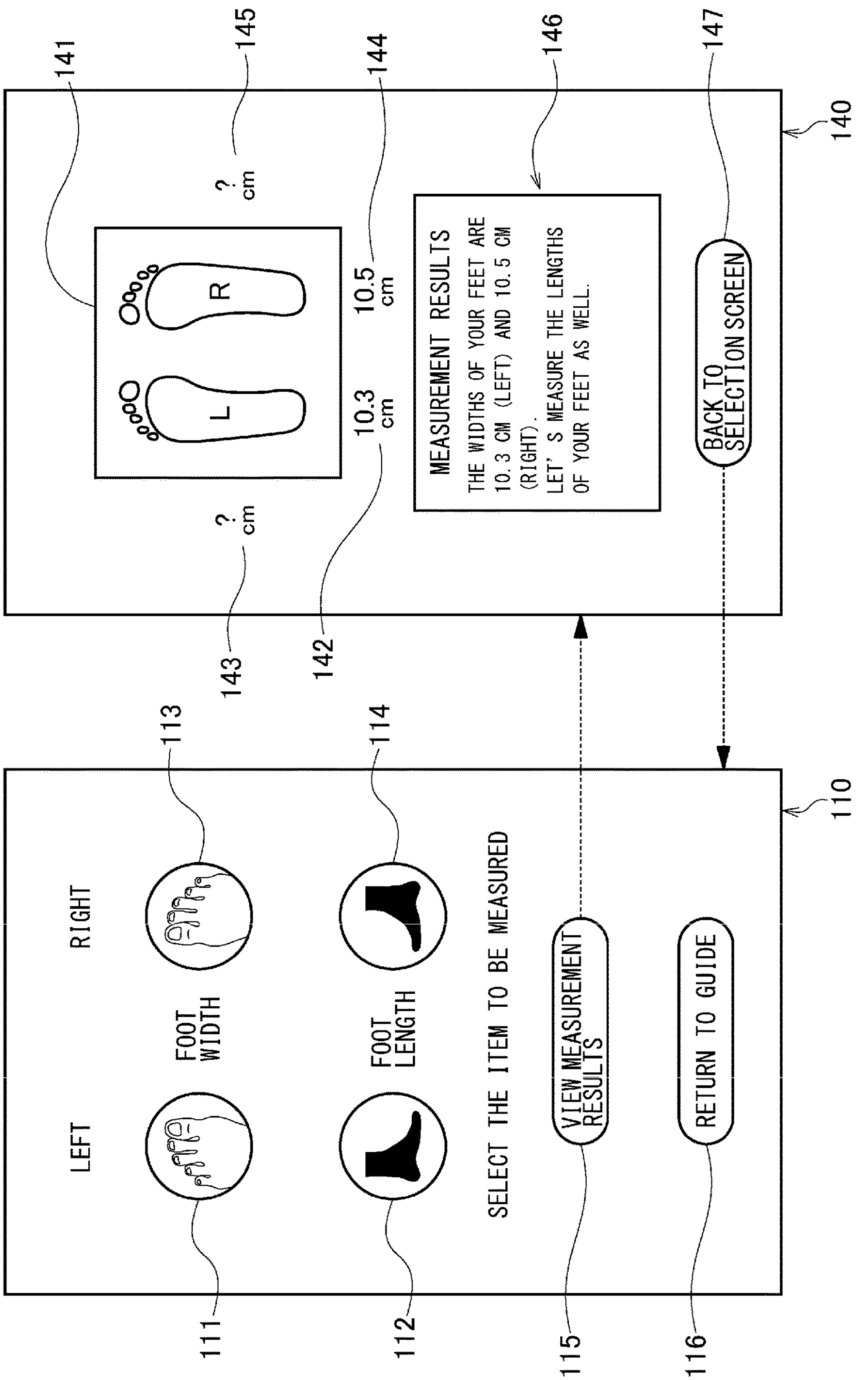
FIG. 8 illustrates the selection screen and the measurement result screen shown after the image shooting for the left and right foot widths is performed.

FIG. 8 illustrates the selection screen and the measurement result screen shown after the image shooting for the left and right foot widths is performed. On the selection screen 110 in FIG. 8, among the four selection buttons, the first element selection button 111 and the third element selection button 113, for which image shooting has been performed, are displayed in the form of thumbnails of the captured images, instead of the pictograms. This allows the measured person to visually recognize that the image shooting for the left and right foot widths has been performed. When the measured person presses the result display button 115, the screen shifts to the measurement result screen 140 shown on the right in FIG. 8.

In the example of the measurement result screen 140 in FIG. 8, since the left and right foot widths have been measured, the foot figure column 141 shows a picture of the left and right feet. Also, with respect to the foot figure column 141, the left foot width column 142 is displayed on the lower left side, the left foot length column 143 is displayed on the left side, a right foot width column 144 is displayed on the lower right side, and a right foot length column 145 is displayed on the right side. Initially, each of the left foot width column 142, the left foot length column 143, the right foot width column 144, and the right foot length column 145 is filled with a unit with no numerical value, such as "? cm", for the foot width or the foot length. After the measurement of each measurement element, for the measured foot width or foot length, the numerical value of the measurement result is displayed in the left foot width column 142, the left foot length column 143, the right foot width column 144, or the right foot length column 145. In the example of FIG. 8, numerical values are displayed such as “10.3 cm” in the left foot width column 142 and “10.5 cm” in the right foot width column 144. At this point, the left and right foot widths have been measured but the foot lengths have not been measured yet, so that the comment column 146 shows a character string, such as “The widths of your feet are 10.3 cm (left) and 10.5 cm (right). Let’s measure the lengths of your feet as well.” However, if the difference between the left and right foot widths is a predetermined value or more (such as two sizes or more), evaluation information such as “The difference between the left and right foot widths is large. Based on your usual shoe selection, try to select a well-balanced size. To confirm the balance, trying shoes on at a physical store is recommended.” may be displayed in the comment column 146 so as to indicate to the measured person that the difference between the left and right foot widths is larger than average. When the measured person presses the back button 147, the screen returns to the selection screen 110 shown on the left in FIG. 8.

On the selection screen 110, when the measured person presses one of the first element selection button 111 and the third element selection button 113, which each indicate that measurement therefor has been performed, the screen shifts to the re-shooting screen for the measurement element corresponding to the pressed button, and the measured person can perform re-shooting and re-measurement. Meanwhile, if the measured person only desires the measurement of the left and right foot widths, the measured person may finish the measurement at this point. In the following, an example of a case will be described in which, subsequent to the measurement of the right foot width, image shooting and measurement for the right foot length is further performed.

Figure 9:
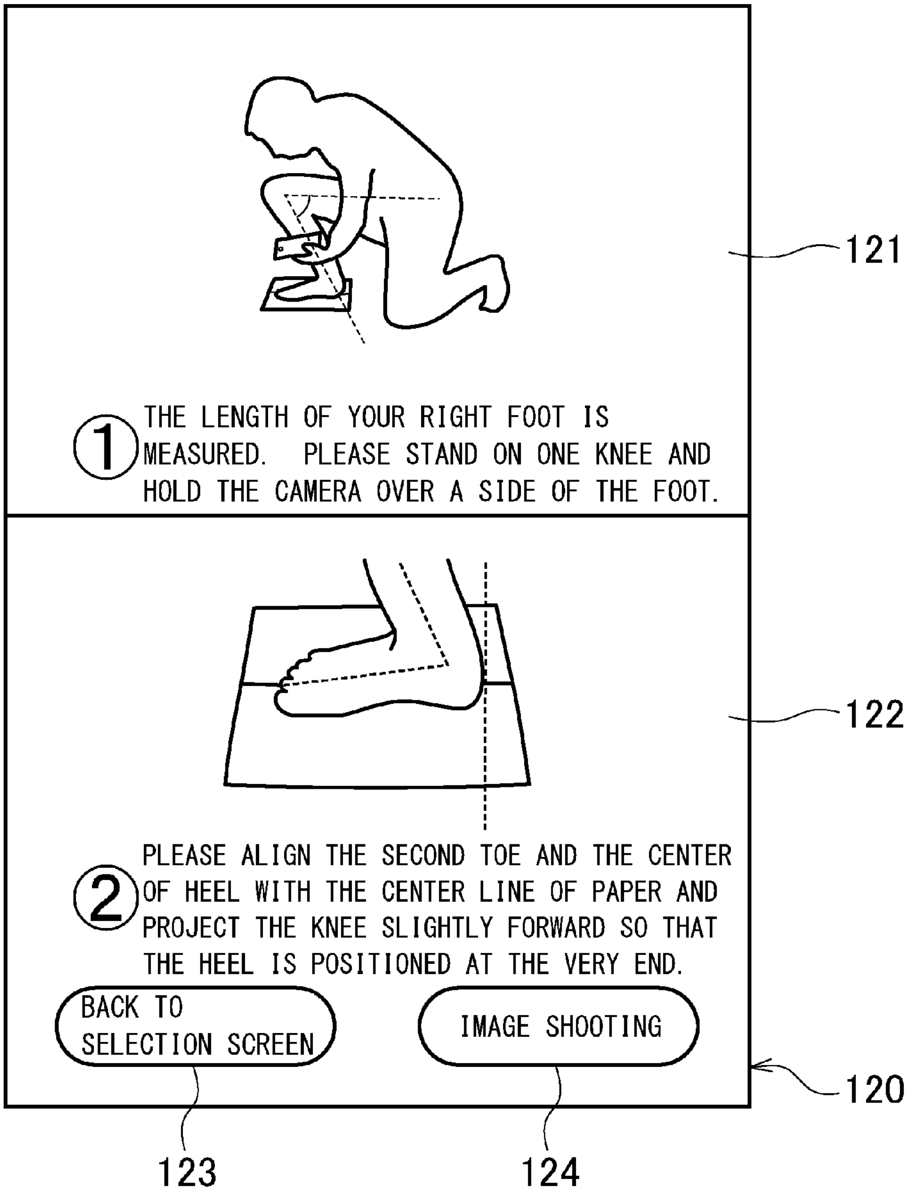
FIG. 9 illustrates an example of a screen for describing a procedure for measuring a right foot length.

FIG. 9 illustrates an example of a screen for describing a procedure for measuring the right foot length. The explanation screen 120 includes the first explanation column 121, the second explanation column 122, the back button 123, and the image shooting shift button 124. The first explanation column 121 shows a character string such as “The length of your right foot is measured. Please stand on one knee and hold the camera over a side of the foot.” and also shows an image illustrating a posture of a measured person for image shooting. The second explanation column 122 shows a character string such as “Please align the second toe and the center of the heel with the center line of the paper and project the knee slightly forward so that the heel is positioned at the very end.” and also shows an image illustrating the positional relationship between the A4 sheet and the foot and the ankle angle. When the measured person presses the back button 123, the image shooting is stopped, and the screen returns to the selection screen 110 shown in FIG. 8. When the measured person presses the image shooting shift button 124, the screen shifts to the image shooting screen shown in FIG. 10. Also when the left foot length is measured, similar explanation is displayed.

Figure 10:
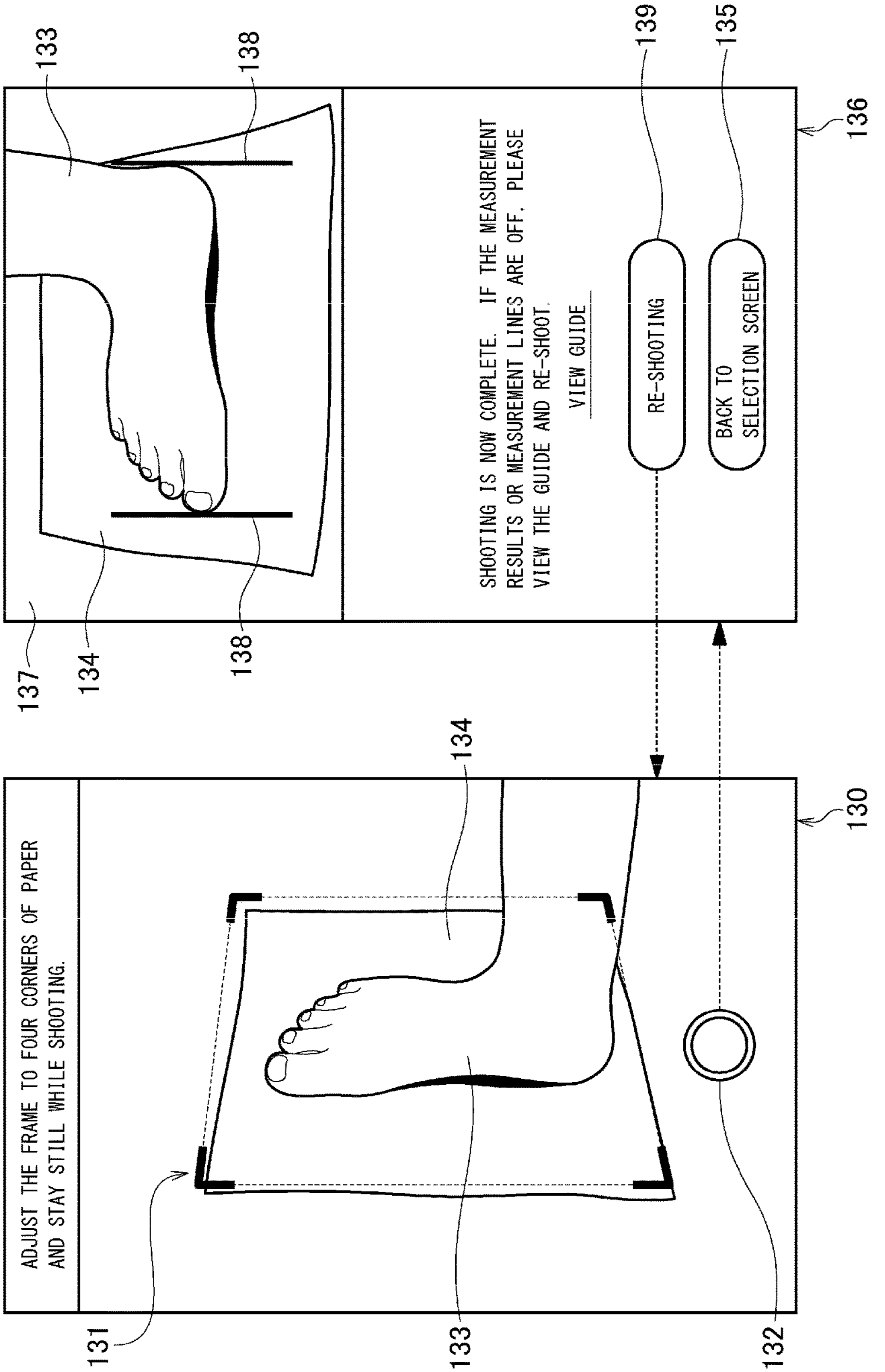
FIG. 10 illustrates the image shooting screen for the right foot length.

FIG. 10 illustrates the image shooting screen for the right foot length. On the entirety of the image shooting screen 130, a live view image captured by the camera of the user terminal 10 is displayed, and, on the live view image, the frame image 131 and the shutter button 132 are superimposed. As the live view image, an image of the foot 133 of the measured person placed on the white paper 134 is displayed on the image shooting screen 130, and the measured person adjusts the distance between the camera and the foot or the angle of view so that the white paper 134 is positioned to almost match the frame image 131. When the measured person presses the shutter button 132, the image acquirer 30 performs shutter operation to acquire a one-foot image, and the screen shifts to the shooting result screen 136 shown on the right in FIG. 10. When the measured person presses the back button 135, the screen returns to the selection screen 110 shown in FIG. 8.

The image acquirer 30 may recognize the shape and the ratio of two sides of the white paper 134 as the reference object on the image and may perform shutter operation to acquire a one-foot image upon recognition of satisfying a predetermined condition indicating that the image contains the reference object of appropriate shape and size. The predetermined condition indicating that the image contains the reference object of appropriate shape and size may be, for example, a condition that defines a trapezoidal shape and a ratio of two sides thereof assumed to be obtained when the white paper 134 as the reference object is shot from diagonally above. Also when the image shooting for the left foot length is performed, similar screens are displayed and image shooting is performed following a similar procedure.

The shooting result screen 136 shows the one-foot image 137 in an upper center part thereof and also shows the measurement support lines 138, which are two vertical lines positioned respectively at the toe and the heel of the foot 133 recognized by the foot length measurer 48 based on the one-foot image 137. When misidentification has occurred in the foot length measurement or when the measured person desires re-shooting for a clearer image, by pressing the re-shooting button 139, the measured person can return to the image shooting screen 130 again to perform re-shooting. When there is no problem with the one-foot image 137, the measured person presses the back button 135 to shift to the selection screen 110 shown in FIG. 8.

Figure 11:
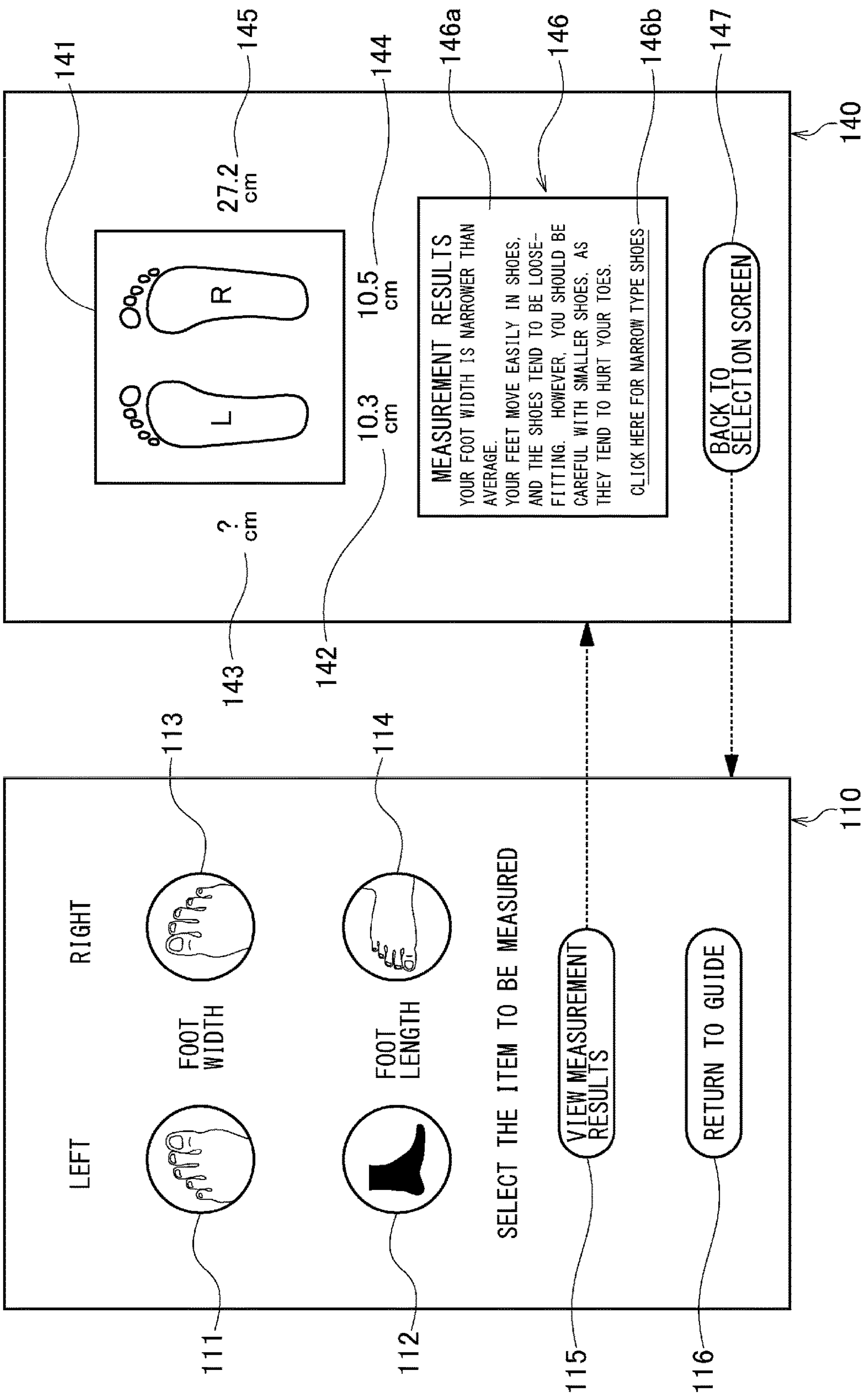
FIG. 11 illustrates the selection screen and the measurement result screen shown after the image shooting for the left and right foot widths and the right foot length is performed.

FIG. 11 illustrates the selection screen and the measurement result screen shown after the image shooting for the left and right foot widths and the right foot length is performed. On the selection screen 110 in FIG. 11, among the four selection buttons, the first element selection button 111, the third element selection button 113, and the fourth element selection button 114, for which image shooting has been performed, are displayed in the form of thumbnails of the captured images, instead of the pictograms. This allows the measured person to visually recognize that the image shooting for the left and right foot widths and the right foot length has been performed. When the measured person presses the result display button 115, the screen shifts to the measurement result screen 140 shown on the right in FIG. 11.

In the example of the measurement result screen 140 in FIG. 11, since the left and right foot widths and the right foot length have been measured, numerical values are displayed such as “10.3 cm” in the left foot width column 142, “10.5 cm” in the right foot width column 144, and “27.2 cm” in the right foot length column 145. At this point, since both the foot width and the foot length have been measured for the right foot, the information generator 50 generates evaluation information regarding the wideness or narrowness of the right foot width with respect to the right foot length when compared to the average. The comment column 146 shows, instead of the content shown in FIG. 8, a character string **146*a* such as “Your foot width is narrower than average. Your feet move easily in shoes, and the shoes tend to be loose-fitting. However, you should be careful with smaller shoes, as they tend to hurt your toes.” The comment column 146 also shows a link to recommended products of shoes designed narrower than the average foot width, in the form of a character string 146***b* such as "Click here for narrow type shoes."

When the foot width is wider than average, the displayed character string is changed to a character string such as "Your foot width is wider than average. Selecting a generous size is recommended, as your foot width, instep, and heel tend to be tight." or "Your foot width is very wider than average. Selecting a size that matches your foot width, with a large margin at the toe, is recommended, as your foot width, instep, and heel tend to be tight." In this case, the comment column 146 also shows a link to recommended products of shoes designed wider than average, with a character string such as "Click here for wide type shoes" or "Click here for extra-wide shoes", and a comment such as "Considering your foot width, a size slightly larger than your foot length-based size is recommended." or "Since your foot width is very wide, a size larger than your foot length-based size is recommended." When the measured person presses the back button 147, the screen returns to the selection screen 110 shown on the left in FIG. 11.

On the selection screen 110, when the measured person presses one of the first element selection button 111, the third element selection button 113, and the fourth element selection button 114, which each indicate that measurement therefor has been performed, the screen shifts to the re-shooting screen for the measurement element corresponding to the pressed button, and the measured person can perform re-shooting and re-measurement. Meanwhile, if the measured person only desires the measurement of the left and right foot widths and the right foot length, the measured person may finish the measurement at this point. In the following, an example of a case will be described in which, subsequent to the measurement of the right foot length, image shooting and measurement for the left foot length is further performed. Since the shooting method for the left foot length is the same as illustrated in FIGS. 9 and 10, the description thereof will be omitted.

Figure 12:
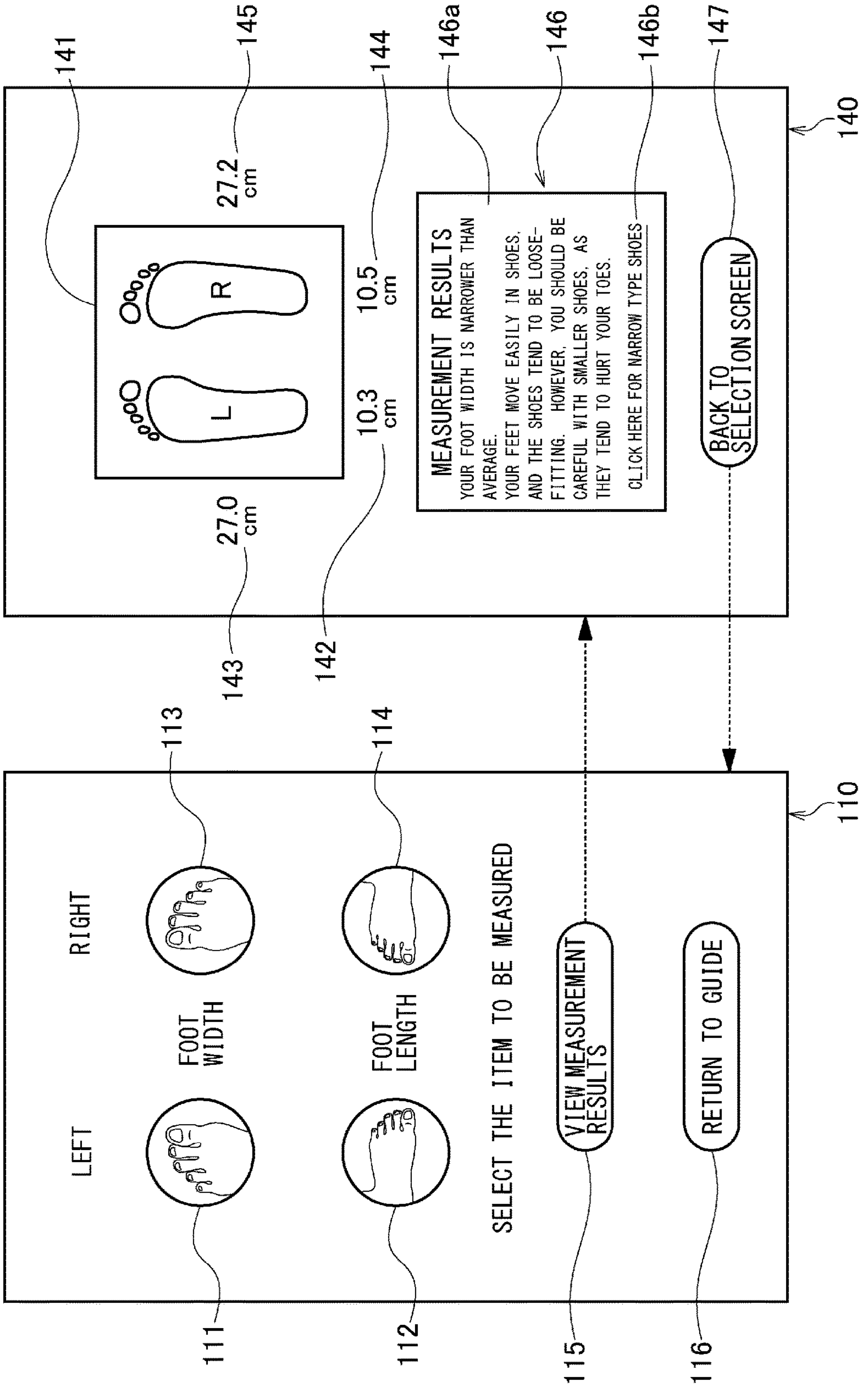
FIG. 12 illustrates the selection screen and the measurement result screen shown after the image shooting for the left and right foot widths and the left and right foot lengths is performed.

FIG. 12 illustrates the selection screen and the measurement result screen shown after the image shooting for the left and right foot widths and the left and right foot lengths is performed. On the selection screen 110 in FIG. 12, all of the four selection buttons of the first element selection button 111, the second element selection button 112, the third element selection button 113, and the fourth element selection button 114 are displayed in the form of thumbnails of the captured images, instead of the pictograms. This allows the measured person to visually recognize that the image shooting for the left and right foot widths and the left and right foot lengths has been performed. When the measured person presses the result display button 115, the screen shifts to the measurement result screen 140 shown on the right in FIG. 12.

In the example of the measurement result screen 140 in FIG. 12, since the left and right foot widths and the left and right foot lengths have been measured, numerical values are displayed such as "10.3 cm" in the left foot width column 142, "27.0 cm" in the left foot length column 143, "10.5 cm" in the right foot width column 144, and "27.2 cm" in the right foot length column 145. If the difference between the left and right foot lengths is a predetermined value or more (such as one size or more), evaluation information such as "There is a difference between your left and right foot lengths. Select a size based on the longer foot." may be displayed in the comment column 146 so as to indicate to the measured person that the difference between the left and right foot lengths is larger than average. When the measured person presses the back button 147, the screen returns to the selection screen 110 shown on the left in FIG. 12.

On the selection screen 110, when the measured person presses one of the first element selection button 111, the second element selection button 112, the third element selection button 113, and the fourth element selection button 114, which each indicate that measurement therefor has been performed, the screen shifts to the re-shooting screen for the measurement element corresponding to the pressed button, and the measured person can perform re-shooting and re-measurement.

Figure 13:
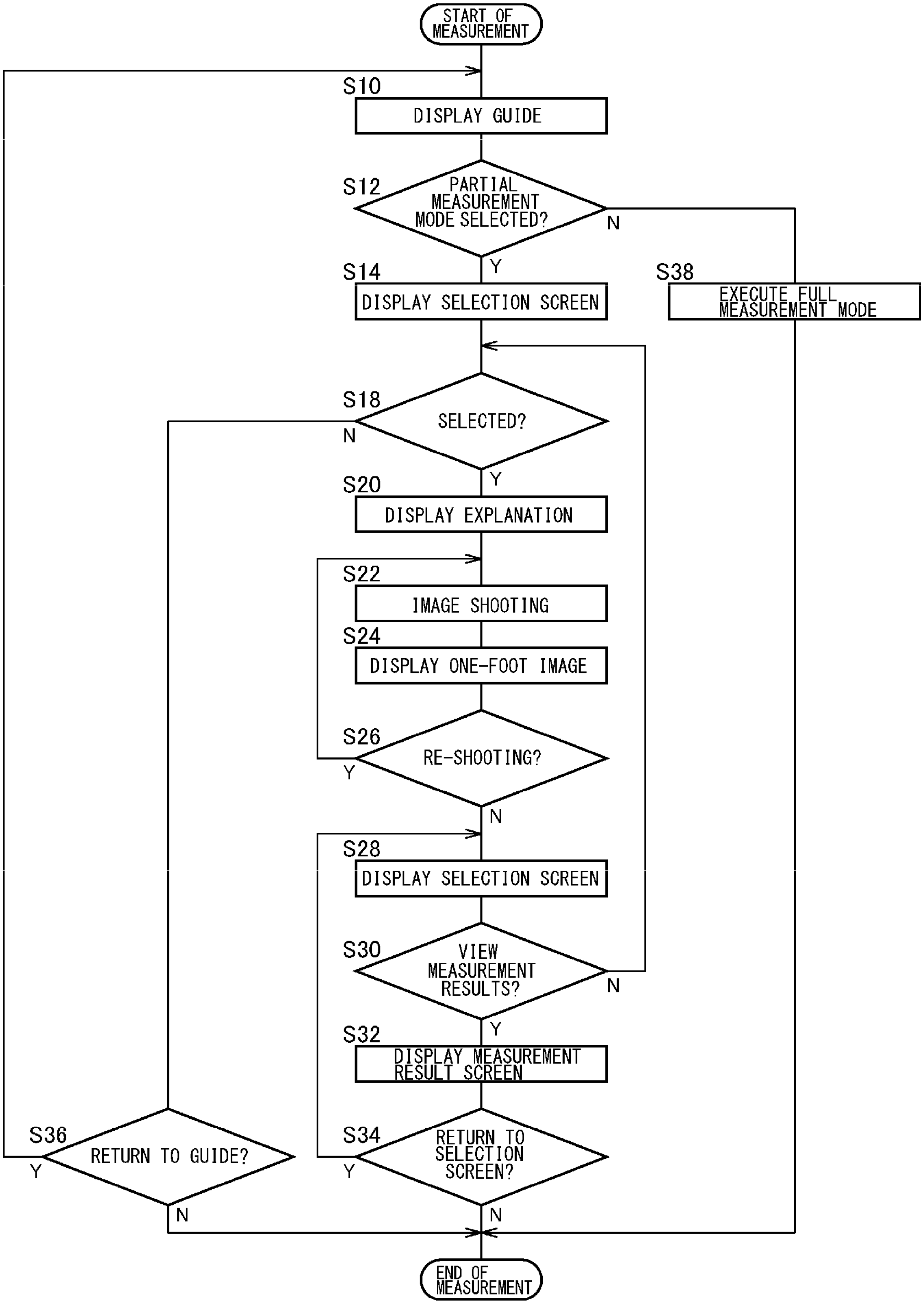
FIG. 13 is a flowchart that shows a foot size measurement process in a partial measurement mode.

FIG. 13 is a flowchart that shows a foot size measurement process in the partial measurement mode. When the measurement process is started, a guide explaining the measurement method is displayed as the start screen 101 shown in FIG. 3 (S10). If the measured person presses the second start button 103 to select the "partial measurement mode" (Y at S12), the selection screen 110 shown in FIG. 4 is displayed (S14). If the measured person presses the first start button 102 to select the "full measurement mode" (N at S12), the full measurement mode is executed (S38).

When the measured person selects, on the selection screen 110 in S14, one of the first element selection button 111, the second element selection button 112, the third element selection button 113, and the fourth element selection button 114 (Y at S18), the explanation screen 120 is displayed (S20), and image shooting is performed on the image shooting screen 130 (S22). After the image shooting, the one-foot image 137 is displayed on the shooting result screen 136 (S24) and, if the measured person selects re-shooting (Y at S26), the process returns to S22 to perform re-shooting. If the measured person does not select re-shooting (N at S26) and returns to the selection screen 110 (S28) and if the measured person presses the result display button 115 (Y at S30), the measurement result screen 140 is displayed (S32). Then, if the back button 147 is pressed (Y at S34), the process returns to S28, and, if the back button 147 is not pressed (N at S 34), the measurement is terminated. In the step S30, if the measured person does not press the result display button 115 (N at S30), the process returns to S18, and, thereafter, the selection of the measurement element to be measured will be repeated. In the step S18, if the selection of the measurement element is not performed (N at S18) and if returning to the guide is selected (Y at S36), the process returns to S10. If the returning to the guide is not selected either (N at S36), the measurement is terminated.

In the present embodiment, one or more of the multiple measurement elements can be selected and measured, and, based on the one or more measurement elements, the foot size information can be generated. Also, some of the measurement elements can be re-measured at arbitrary timing. Accordingly, even when measuring only some of the measurement elements is sufficient or even when a measurement error has occurred in only some of the measurement elements, measuring all the measurement elements from the beginning is unnecessary. Therefore, the efficiency of the foot size measurement can be improved.

The present disclosure has been described with reference to an embodiment. The embodiment is intended to be illustrative only, and it will be obvious to those skilled in the art that various modifications to a combination of constituting elements or processes could be developed and that such modifications also fall within the scope of the present disclosure.

What is claimed is:

1. A foot size measurement device comprising:

a camera;

a memory storing computer-readable instructions which, when executed, cause the foot size measurement device to perform a foot size measurement method; and a processor which, when executing the computer-readable instructions, is configured to control the foot size measurement device to perform the foot size measurement method, the foot size measurement method including:

controlling the camera to capture a first image of a foot of a measured person and a reference object from a first view above the foot and the reference object;

determining a first width of the foot of the measured person based on a ratio between dimensions of the reference object and the foot of the measured person in the first image;

controlling the camera to capture a second image of the foot of the measured person and the reference object from a second view over a medial side of the foot of the measured person and the reference object;

determining a first length of the foot of the measured person based on the ratio between the dimensions of the reference object and the foot of the measured person in the second image;

controlling, in response to determining the first width of the foot of the measured person and the first length of the foot of the measured person, the foot size measurement device to display first foot size information of the foot of the measured person based on the first width of the foot of the measured person and the first length of the foot of the measured person;

controlling the camera to capture only one of a third image of the foot of the measured person and the reference object from the first view or a fourth image of the foot and the reference object from the second view;

determining one of a second width of the foot of the measured person based on the ratio between the dimensions of the reference object and the foot of the measured person in the third image or a second length of the foot of the measured person based on the ratio between the dimensions of the reference object and the foot of the measured person in the fourth image; and controlling, in response to determining the second width of the foot of the measured person or the second length of the foot of the measured person, the foot size measurement device to display second foot size information of the foot of the measured person that is an update from the first foot size information based on the second width of the foot of the measured person or the second length of the foot of the measured person.

2. The foot size measurement device according to claim 1, wherein the first foot size information includes content that depends on a combination of the first width of the foot of the measured person and the first length of the foot of the measured person.

3. The foot size measurement device according to claim 1, wherein the foot size measurement method further comprises:

in response to determining the first width of the foot of the measured person, controlling the foot size measurement device to display only the first width of the foot of the measured person; and in response to determining the first length of the foot of the measured person, controlling the foot size measurement device to display only the first length of the foot of the measured person.

4. The foot size measurement device according to claim 2, wherein the foot size measurement method further comprises:

in response to determining the first width of the foot of the measured person, controlling the foot size measurement device to display only the first width of the foot of the measured person; and in response to determining the first length of the foot of the measured person, controlling the foot size measurement device to display only the first length of the foot of the measured person.

5. A foot size measurement method comprising:

capturing a first image of a foot of a measured person and a reference object from a first view above the foot and the reference object;

determining a first width of the foot of the measured person based on a ratio between dimensions of the reference object and the foot of the measured person in the first image;

capturing a second image of the foot of the measured person and the reference object from a second view over a medial side of the foot of the measured person and the reference object;

determining a first length of the foot of the measured person based on the ratio between the dimensions of the reference object and the foot of the measured person in the second image;

in response to determining the first width of the foot of the measured person and the first length of the foot of the measured person, displaying first foot size information of the foot of the measured person based on the first width of the foot of the measured person and the first length of the foot of the measured person;

capturing only one of a third image of the foot of the measured person and the reference object from the first view or a fourth image of the foot and the reference object from the second view;

determining one of a second width of the foot of the measured person based on the ratio between the dimensions of the reference object and the foot of the measured person in the third image or a second length of the foot of the measured person based on the ratio between the dimensions of the reference object and the foot of the measured person in the fourth image; and in response to determining the second width of the foot of the measured person or the second length of the foot of the measured person, displaying second foot size information of the foot of the measured person that is an update from the first foot size information based on the second width of the foot of the measured person or the second length of the foot of the measured person.

6. A non-transitory computer-readable storage medium storing a foot size measurement program causing a computer to implement a foot size measurement method, the foot size measurement method comprising:

capturing a first image of a foot of a measured person and a reference object from a first view above the foot and the reference object;

determining a first width of the foot of the measured person based on a ratio between dimensions of the reference object and the foot of the measured person in the first image;

capturing a second image of the foot of the measured person and the reference object from a second view over a medial side of the foot of the measured person and the reference object;

determining a first length of the foot of the measured person based on the ratio between the dimensions of the reference object and the foot of the measured person in the second image;

in response to determining the first width of the foot of the measured person and the first length of the foot of the measured person, displaying first foot size information of the foot of the measured person based on the first width of the foot of the measured person and the first length of the foot of the measured person;

capturing only one of a third image of the foot of the measured person and the reference object from the first view or a fourth image of the foot and the reference object from the second view;

determining one of a second width of the foot of the measured person based on the ratio between the dimensions of the reference object and the foot of the measured person in the third image or a second length of the foot of the measured person based on the ratio between the dimensions of the reference object and the foot of the measured person in the fourth image; and in response to determining the second width of the foot of the measured person or the second length of the foot of the measured person, displaying second foot size information of the foot of the measured person that is an update from the first foot size information based on the second width of the foot of the measured person or the second length of the foot of the measured person.

7. The foot size measurement device according to claim 1, wherein the second view includes a positional relationship between the reference object, the foot of the measured person, and an ankle angle of the measured person standing on one knee.

8. The foot size measurement method according to claim 5, wherein the second view includes a positional relationship between the reference object, the foot of the measured person, and an ankle angle of the measured person standing on one knee.

9. The non-transitory computer-readable storage medium according to claim 6, wherein the second view includes a positional relationship between the reference object, the foot of the measured person, and an ankle angle of the measured person standing on one knee.

* * * * *